United States Patent
Stack et al.

(10) Patent No.: US 6,815,448 B2
(45) Date of Patent: Nov. 9, 2004

(54) AZAHETEROCYCLYLMETHYL DERIVATIVES OF 7,8-DIHYDRO-1,6,9-TRIOXA-3-AZA-CYCLOPENTA[A] NAPHTHALENE AS 5-$HT_{1A}$ ANTAGONISTS

(75) Inventors: Gary P. Stack, Ambler, PA (US); Megan Tran, Hoboken, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/132,237

(22) Filed: Apr. 25, 2002

(65) Prior Publication Data

US 2002/0193365 A1 Dec. 19, 2002

Related U.S. Application Data

(60) Provisional application No. 60/289,168, filed on May 7, 2001.

(51) Int. Cl.[7] ................... C07D 498/04; C07D 519/00; A61K 31/424; A61P 25/28
(52) U.S. Cl. ................... 514/278; 514/338; 514/375; 546/20; 546/217.7; 548/218
(58) Field of Search ................... 514/278, 338, 514/375; 546/20, 271.7; 548/218

(56) References Cited

U.S. PATENT DOCUMENTS

| | | | |
|---|---|---|---|
| 5,318,988 A | 6/1994 | Schohe-Loop et al. | 514/458 |
| 5,371,094 A | 12/1994 | Heine et al. | 514/323 |
| 5,869,490 A | 2/1999 | Stack | 514/255 |
| 6,525,075 B2 * | 2/2003 | Tran et al. | 514/338 |

FOREIGN PATENT DOCUMENTS

| WO | WO 91/13872 | 9/1991 |
|---|---|---|
| WO | WO 97/23485 | 7/1997 |
| WO | WO 98/29415 | 7/1998 |
| WO | WO 98/40386 | 9/1998 |

OTHER PUBLICATIONS

Robichaud et al. (Annual reports in Medicinal Chemistry 35, Chapter 2) 2000.*
Saxena et al. (Pharmac. Ther. vol. 66, pp. 339–368, 1995).*
Carl Boast et al., Neurobiol. of Learning and Memory, 1999, 259–271, 71(3).
M. Carli et al., Neuropharmacology, 1999, 1165–1173, 38(8).
Alfredo Meneses et al., Neurobiol. of Learning and Memory, 1999, 207–218, 71(2).

* cited by examiner

*Primary Examiner*—Bruck Kifle
(74) *Attorney, Agent, or Firm*—Woodcock Washburn LLP

(57) ABSTRACT

Compounds of the formula

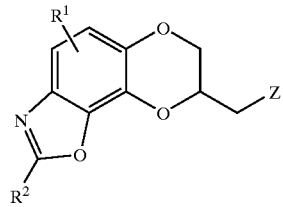

are useful for treating the cognitive deficits due to aging, stroke, head trauma, Alzheimer's disease or other neurodegenerative diseases, or schizophrenia. The compounds of the invention are also useful for the treatment of disorders such as anxiety, aggression and stress, and for the control of various physiological phenomena, such as appetite, thermoregulation, sleep and sexual behavior.

29 Claims, No Drawings

AZAHETEROCYCLYLMETHYL DERIVATIVES OF 7,8-DIHYDRO-1,6,9-TRIOXA-3-AZA-CYCLOPENTA[A] NAPHTHALENE AS 5-HT$_{1A}$ ANTAGONISTS

This application claims priority from provisional application Ser. No. 60/289,168, filed on May 7, 2001, the entire disclosure of which is hereby incorporated by reference.

BACKGROUND OF THE INVENTION

Recent studies with the selective 5-HT$_{1A}$ antagonist WAY-100635 have confirmed a role for 5-HT$_{1A}$ receptors in learning and memory. Carli et. al. (Neuropharmacology (1999), 38(8), 1165–1173) demonstrated that WAY-100635 prevented the impairment of spatial learning caused by intrahippocampal injection of 3-[(R)-2-carboxypiperazin-4-yl]propyl-1-phosphonic acid (CPP), a competitive NMDA receptor antagonist, in a two-platform spatial discrimination task. Boast et. al. (Neurobiol. Learn. Mem. (1999), 71(3) 259–271) found that WAY-100635 significantly reduced the cognitive impairment induced by the non-competitive NMDA antagonist MK801, as determined by the performance of rats trained on a delayed nonmatching to sample radial arm maze task. Menesis et al. (Neurobiol. Learn. Mem. (1999), 71(2) 207–218) showed that post-training administration of WAY-100635 reversed the learning deficit induced by scopolamine, a cholinergic antagonist, in an autoshaping learning task. New, novel 5-HT$_{1A}$ antagonists would be useful for these and other uses.

DESCRIPTION OF THE INVENTION

In accordance with this invention, there is provided a group of novel compounds of the formula I:

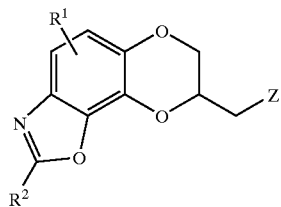

I wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidine, piperidine, homopiperidine, morpholine, thiomorpholine,

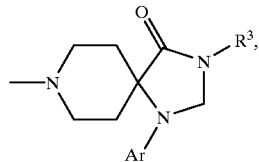

II

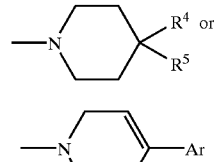

III

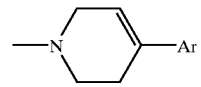

IV $R^3$ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl, each optionally substituted;

$R^4$ is hydroxy, cyano or carboxamido and $R^5$ is Ar; or $R^4$ is hydrogen and $R^5$ is benzoyl, 1-benzimidazol-2-one, benzoisothiazole, benzisoxazole, each optionally substituted, or —(CH$_2$)$_m$Q;

m is 0 to 4; and

Q is Ar,

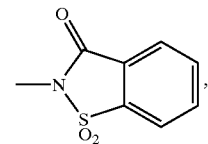

V

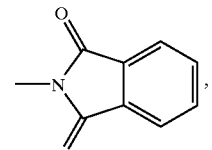

VI

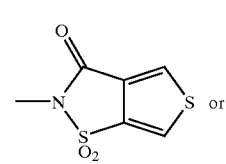

VII

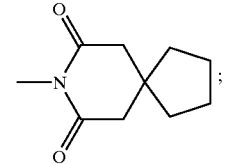

VIII or a pharmaceutically acceptable salt thereof.

It is preferred in some embodiments of the invention that Z is a radical of formula II or III.

In some preferred embodiments of the invention $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atom; and Z is a radical of formula II. More preferably, $R^1$ is hydrogen, halo, trifluoromethyl, alkyl of one to six carbon atoms or alkoxy of one to six carbon atoms; and $R^2$ is hydrogen, trifluoromethyl or alkyl of one to six carbon atom.

In other preferred embodiments of the invention $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atom; and Z is a radical of formula III. More preferably, $R^1$ is hydrogen, halo, trifluoromethyl, alkyl of one to six carbon atoms or alkoxy of one to six carbon atoms; and $R^2$ is hydrogen, trifluoromethyl or alkyl of one to six carbon atom.

In still other embodiments of the invention, $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atom; and Z is a radical of formula IV, $R^4$ is hydroxy and $R^5$ is Ar. More preferably, $R^1$ is hydrogen, halo, trifluoromethyl, alkyl of one to six carbon atoms or alkoxy of one to six carbon atoms; and $R^2$ is hydrogen, trifluoromethyl or alkyl of one to six carbon atom.

In further embodiments of the invention $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atom; Z is a radical of formula IV, $R^4$ is hydrogen and $R^5$ is benzoyl, 1-benzimidazol-2-one, benzoisothiazole, or benzisoxazole, each optionally substituted, or —$(CH_2)_m$Q. More preferably, $R^1$ is hydrogen, halo, trifluoromethyl, alkyl of one to six carbon atoms or alkoxy of one to six carbon atoms; and $R^2$ is hydrogen, trifluoromethyl or alkyl of one to six carbon atom, and m is 0 or 1.

Where a substituent is "substituted" as used herein it may include from 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

This invention relates to both the R and S stereoisomers of the 8-aminomethyl-7,8-dihydro-1,6,9-trioxa-3-aza-cyclopenta[a]naphthalene, as well as to mixtures of the R and S stereoisomers. Throughout this application, the name of the product of this invention, where the absolute configuration of the 8-aminomethyl-7,8-dihydro-1,6,9-trioxa-3-aza-cyclopenta[a]naphthalene is not indicated, is intended to embrace the individual R and S enantiomers as well as mixtures of the two. In some preferred embodiments of the present invention the S stereoisomer is preferred.

Where a stereoisomer is preferred, it may, in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free, as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or prepared by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl, as used herein refers to an aliphatic hydrocarbon chain and includes straight and branched chains such as methyl, ethyl, n-propyl, isopropyl, n-butyl, isobutyl, sec-butyl, t-butyl, n-pentyl, isopentyl, neo-pentyl, n-hexyl, and isohexyl. Lower alkyl refers to alkyl having 1 to 3 carbon atoms.

Alkanamido as used herein refers to the group R—C(=O)—NH— where R is an alkyl group of 1 to 5 carbon atoms.

Alkanoyloxy as used herein refers to the group R—C(=O)—O— where R is an alkyl group of 1 to 5 carbon atoms.

Alkanesulfonamido as used herein refers to the group R—S(O)$_2$—NH— where R is an alkyl group of 1 to 6 carbon atoms.

Alkoxy as used herein refers to the group R—O— where R is an alkyl group of 1 to 6 carbon atoms.

Carboxamido, as used herein refers to the group —CO—NH$_2$.

Carboalkoxy as used herein refers to the group R—O—C(=O)— where R is an alkyl group of 1 to 5 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific compounds of the present invention are:

8-(2-methyl-7,8-dihydro-1,6,9-trioxa-3-aza-cyclopenta[a]naphthalen-8-ylmethyl)-1-phenyl-1,3,8-triazaspiro[4.5]decan-4-one;

1-[1-(2-methyl-7,8-dihydro-1,6,9-trioxa-3-aza-cyclopenta[a]naphthalen-8-ylmethyl)-piperidin-4-yl]-1,3-dihydro-2H-benzimidazol-2-one;

1-(2-methyl-7,8-dihydro-1,6,9-trioxa-3-aza-cyclopenta[a]naphthalen-8-ylmethyl)-4-[3-(trifluoromethyl)phenyl]-4-piperidinol;

(4-fluorophenyl) (1-[2-methyl-7,8-dihydro-1,6,9-trioxa-3-aza-cyclopenta[a]-naphthalen-8-ylmethyl]-4-piperidinyl) methanone;

2-methyl-8-{[4-(3-trifluoromethyl)phenyl-3,6-dihydro-1(2H)-pyridinyl]methyl}-7,8-dihydro-1,6,9-trioxa-3-aza-cyclopenta[a]naphthalene; and 2-methyl-8-(piperidin-1-ylmethyl)-7,8-dihydro-1,6,9-trioxa-3-aza-cyclopenta-[a]naphthalene or pharmaceutically acceptable salts thereof.

The 8-azaheterocyclylmethyl-7,8-dihydro-1,6,9-trioxa-3-aza-cyclopenta[a]-naphthalenes of the invention are prepared as illustrated below. Specifically, the appropriately substituted nitroguaiacol is alkylated with allyl bromide in the presence of a suitable base such as sodium hydride and then demethylated by a reagent such as sodium hydroxide. The resulting 4-nitro-2-allyloxyphenol is then alkylated with glycidyl tosylate or an epihalohydrin in the presence of a base such as sodium hydride and heated in a high boiling solvent such as mesitylene or xylene to effect both rearrangement of the allyl group and cyclization of the dioxan ring. The resulting primary alcohol is converted to the tosylate by reaction with p-toluenesulfonyl chloride in the presence of a tertiary amine or pyridine or alternatively to a halide by reaction with carbon tetrabromide or carbon tetrachloride in combination with triphenylphosphine. The allyl side chain is then isomerized by treatment with catalytic bis-acetonitrile

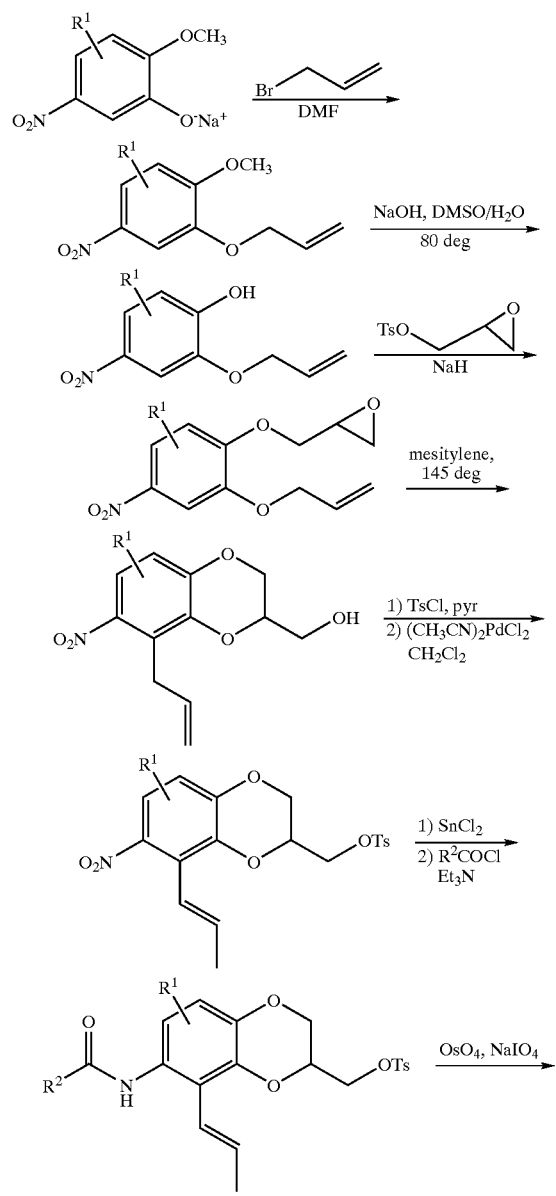

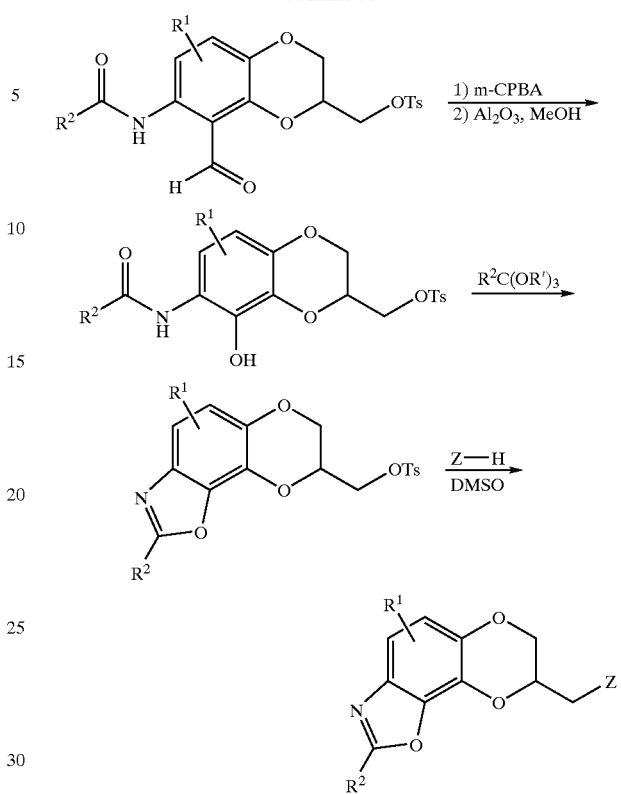

palladium (II) chloride in refluxing methylene chloride or benzene and the nitro group reduced to the aniline with a suitable reducing agent such as tin (II) chloride. The aniline is then acylated with the appropriate acyl halide or anhydride and the olefin cleaved to the corresponding o-amidobenzaldehyde by treatment with catalytic osmium tetroxide in the presence of sodium periodate. The aldehyde is converted to the phenol by treatment with meta-chloroperoxybenzoic acid in a Baeyer-Villager reaction and cyclization to the 7,8-dihydro-1,6,9-trioxa-3-aza-cyclopenta[a]-naphthalene is effected by treatment at reflux with an appropriate dehydrating agent such as an ortho ester. Replacement of the tosylate or halide with the appropriately substituted azaheterocycle (Z—H) in some high boiling solvent such as dimethyl sulfoxide gives the title compounds of the invention.

Alternatively, the aniline produced by the tin (II) chloride reduction described above may be protected by a suitable protecting group such as carbobenzoxy (Cbz) before the olefin is cleaved to the aldehyde by treatment with osmium tetroxide/sodium periodate and the aldehyde converted to a phenol by the Baeyer-Villager procedure. Deprotection by treatment with hydrogen over palladium on carbon gives the o-aminophenol, which is cyclized to the 7,8-dihydro-1,6,9-trioxa-3-aza-cyclopenta[a]naphthalene by treatment with the appropriate ortho ester, carboxylic acid or anhydride. Treatment of the o-aminophenol

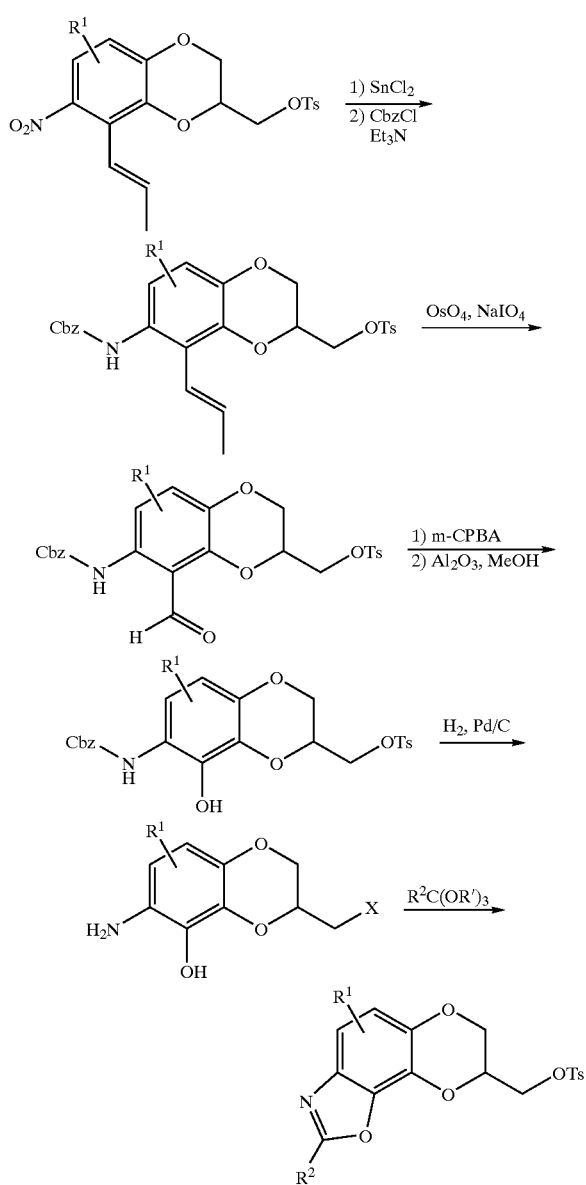

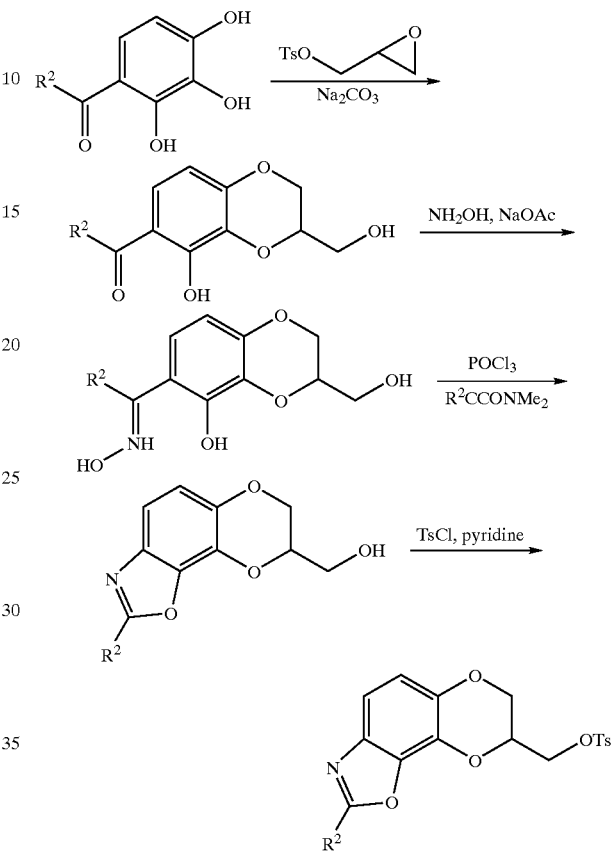

with cyanogen bromide or chloride or a suitably substituted carbamoyl chloride leads to compounds of the invention in which $R^2$ is amino. Treatment of the o-aminophenol with carbonyl diimidazole gives the oxazolone which leads to compounds of the invention in which $R^2$ is halo via treatment with an inorganic anhydride such as phosphoryl chloride or bromide, or to compounds of the invention in which $R^2$ is alkoxy by treatment with the appropriate alkylating agent. Replacement of the tosylate with the appropriately substituted azaheterocycle as above gives the title compounds of the invention.

Compounds of the invention in which $R^1$ is hydrogen and $R^2$ is alkyl are most conveniently prepared according to the scheme below. The appropriate 2',3',4'-trihydroxyacylphenone is regioselectively alkylated with glycidyl tosylate or an epihalohydrin in the presence of a base such as sodium carbonate to give the corresponding 7-acyl-8-hydroxybenzodioxan-2-methanol. Following conversion of the ketone to the oxime by reaction with hydroxylamine hydrochloride and sodium acetate, cyclization to the oxazole is effected by treatment with phosphoryl chloride in the appropriate dimethylalkanoic acid amide. The resulting 7,8-dihydro-1,6,9-trioxa-3-aza-cyclopenta[a]naphthalene-8-methanol is converted to the tosylate by treatment with p-toluenesulfonyl chloride in pyridine and combined with the appropriate azaheterocycles as described to give the title compounds of the invention.

The guaiacols, 2',3',4'-trihydroxyacylphenones and azaheterocycles appropriate to the above chemistry are known compounds or can be prepared by one schooled in the art. The compounds of the invention may be resolved into their enantiomers by conventional methods or, preferably, the individual enantiomers may be prepared directly by substitution of (2R)-(−)-glycidyl 3-nitrobenzenesulfonate or tosylate (for the S benzodioxan methanamine) or (2S)-(+)-glycidyl 3-nitro-benzenesulfonate or tosylate (for the R enantiomer) in place of epihalohydrin or racemic glycidyl tosylate in the procedures above.

High affinity for the serotonin 5-$HT_{1A}$ receptor was established by testing the claimed compound's ability to displace [$^3$H] 8-OH-DPAT (dipropylaminotetralin) from the 5-$HT_{1A}$ serotonin receptor following a modification of the procedure of Hall et al. J. Neurochem. 44, 1685 (1985) which utilizes CHO cells stably transfected with human 5-$HT_{1A}$ receptors. The 5-$HT_{1A}$ affinities for the compounds of the invention are reported below as $K_i$'s.

Antagonist activity at 5-$HT_{1A}$ receptors was established by using a $^{35}$S-GTPγS binding assay similar to that used by Lazareno and Birdsall (Br. J. Pharmacol. 109: 1120, 1993), in which the test compound's ability to affect the binding of $^{35}$S-GTPγS to membranes containing cloned human 5-$HT_{1A}$ receptors was determined. Agonists produce an increase in binding whereas antagonists produce no increase but rather reverse the effects of the standard agonist 8-OH-DPAT. The test compound's maximum inhibitory effect is represented as the $I_{max}$, while its potency is defined by the $IC_{50}$.

The results of the two standard experimental test procedures described in the preceding two paragraphs were as follows:

| Compound | 5-HT$_{1A}$ Receptor Affinity KI (nM) | 5-HT$_{1A}$ Function IC$_{50}$ (nM) (I$_{max}$) |
|---|---|---|
| Example 1 | 0.93 | 1055.0 (60.0) |
| Example 2 | 1.00 | 2.70 (42.0) |
| Example 3 | 6.52 | 47.0 (47.0) |
| Example 4 | 201.75 | — |
| Example 5 | 39.43 | 798.0 (97.0) |
| Example 6 | 172.65 | — |

The compounds of this invention have potent affinity for and antagonist activity at brain 5-HT$_{1A}$ serotonin receptors. The compounds of the invention are thus exceedingly interesting the treatment of cognitive dysfunction such as is associated with mild cognitive impairment (MCI)) Alzheimer's disease and other dementias including Lewy Body, vascular, and post stroke dementias. Cognitive dysfunction associated with surgical procedures, traumatic brain injury or stroke may also be treated in accordance with the present invention. Further, compounds of the present invention may be useful for the treatment of diseases in which cognitive dysfunction is a co-morbidity such as, for example, Parkinson's disease, autism and attention deficit disorders.

Compounds of the present invention are also useful for treating cognitive deficits due to CNS disorders such as schizophrenia, (and other psychotic disorders such as paranoia and mano-depressive illness). The compounds are also useful for the treatment of disorders related to excessive serotonergic stimulation such as anxiety (e.g. generalized anxiety disorders, panic attacks, and obsessive compulsive disorders), aggression and stress. In addition, compounds of the present invention may be useful for the treatment of various physiological conditions such as Tourette's syndrome, migraine, autism, attention deficit disorders and hyperactivity disorders, sleep disorders, social phobias, pain, thermoregulatory disorders, endocrine disorders, urinary incontinence, vasospasm, stroke, eating disorders such as for example obesity, anorexia and bulimia, sexual dysfunction, and the treatment of alcohol, drug and nicotine withdrawal which are known to be, at least in part, under serotonergic influence. Finally, recent clinical trials employing drug mixtures (e.g. fluoxetine and pindolol) have demonstrated a more rapid onset of antidepressant efficacy for a treatment combining SSRI (serotonin selective reuptake inhibitor) activity and 5HT1A antagonism (Blier and Bergeron, 1995; F Artigas, et al., 1996, M. B. Tome et al., 1997). The compounds of the invention are thus interesting and useful as augmentation therapy in the treatment of depressive illness.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

The present invention also provides methods of augmenting the treatment of depression by providing a mammal, preferably a human, with an antidepressant amount of a serotonin selective reuptake inhibitor (such as, but not limited to, sertraline, fluvoxamine, paroxetine, venlafaxine, duloxetine, citalopram, fluoxetine and metabolites thereof) and an amount of a compound of Formula I sufficient to hasten the onset of antidepressant efficacy.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

Compounds of the present invention may further be provided in combination with an antidepressant amount of a serotonin selective reuptake inhibitor to increase the onset of antidepressant efficacy.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 10 mg per day with gradual increase in the daily dose to about 200 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug", as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention.

Intermediate 1

3-Allyloxy-4-methoxynitrobenzene 97.5 g (0.51 mole) of the sodium salt of 5-nitroguaiacol was dissolved in one liter of DMF and 1.5 equivalents of allyl bromide added. The reaction was heated to 65° C. for two hours, after which time much of the dark color had discharged and tlc (1:1 $CH_2Cl_2$/hexane) indicated loss of starting material. The solvent was concentrated in vacuum and the residue washed with water. The product was isolated by filtration and dried in a vacuum. This gave 112 g of pale yellow solid. A sample recrystallized from methanol, gave m.p. 93–94° C.

Intermediate 2

2-Allyloxy-4-nitrophenol

To one liter of dimethyl sulfoxide was added 750 mL of 2 N aqueous sodium hydroxide and the mixture was heated to 65° C. The pale yellow solid 3-allyloxy-4-methoxynitrobenzene prepared above was added in portions over a 30 minute period and then the temperature was raised to 95° C. and maintained for 3 hours, after which time the starting material had been consumed. The mixture was allowed to cool and poured into a mixture of 1 L ice and 1 L 2 N HCl. 73 Grams of crude but homogeneous (by tlc 1:1 $CH_2Cl_2$/hexane) desired product was isolated as a light brown solid by filtration. This material was subsequently dissolved in 1:1 hexane/methylene chloride and filtered through silica gel to give 68 g of pale yellow solid, which, when recrystallized from ethyl/acetate/hexane, gave m.p. 61–62° C. The aqueous mother liquors from the initial crystallization above were extracted with 2 L of ethyl acetate. This was dried over sodium sulfate, filtered and evaporated to a dark oil. Column chromatography on silica with 1:1 $CH_2Cl_2$/hexane gave an additional 12 g of the title compound as a yellow solid. Elution with 2% MeOH in $CHCl_3$ gave 12 g of a dark oil which slowly crystallized in vacuum. This proved to be the Claisen product, 3-allyl-4-nitrocatechol.

Intermediate 3

2-(2-Allyloxy-4-nitrophenoxymethyl)-oxirane 20 g (0.50 mole) of 60% NaH/mineral oil was placed in a two liter flask and washed with 500 mL of hexane. 1 L of DMF was added, followed by 77 g (0.40 mole) of the 2-allyloxy-4-nitrophenol prepared in the previous step. Addition of the phenol was performed in portions under argon. After stirring the mixture for 30 minutes at room temperature under argon, 108 g (0.48 moles) of (R)-glycidyl tosylate was added and the mixture heated at 70–75° C. under nitrogen overnight. Upon cooling, the DMF was removed in vacuum and replaced with one liter of methylene chloride. This was washed with 500 mL portions of 2 N HCl, saturated sodium bicarbonate and saturated brine and dried over sodium sulfate. The mixture was filtered, concentrated to an oil in vacuum and column chromatographed on silica gel using 1:1 hexane/methylene chloride as eluant. This gave 43 g of product contaminated with traces of the two starting materials, followed by 21 g of pure product as a pale yellow solid. The impure material was recrystallized from 1.2 L of 10% ethyl acetate/hexane to give 34 g of pure (homogeneous on silica gel tlc with 1:1 hexane/methylene chloride) (R)-2-(2-allyloxy-4-nitrophenoxymethyl)-oxirane (m.p. 64° C.).

Elemental Analysis for: $C_{12}H_{13}NO_5$ Calc'd: C, 57.37; H, 5.21; N, 5.58 Found: C, 57.50; H, 5.21; N; 5.43

Intermediate 4

(8-Allyl-7-nitro-2,3-dihydro-benzo(1,4)dioxin-2-yl)-methanol (R)-2-(2-Allyloxy-4-nitrophenoxymethyl)-oxirane (20 g, 80 mmoles) prepared as above was heated at 155° C. in mesitylene for 24 hours under nitrogen. Filtration of the black solid which formed gave 1.5 g of very polar material. Evaporation of the solvent in vacuum followed by column chromatography on silica gel with methylene chloride as eluant gave 10 g of recovered starting material and 7.5 g of the desired rearranged (S)-(8-allyl-7-nitro-2,3-dihydro-benzo(1,4)dioxin-2-yl)-methanol, which slowly crystallized on standing in vacuum (m.p. 67° C.). The yield based on recovered starting material is 75%.

Elemental Analysis for: $C_{12}H_{13}NO_5$ Calc'd: C, 57.37; H, 5.21; N, 5.58 Found: C, 57.26; H, 5.20; N, 5.35

Intermediate 5

Toluene-4-sulfonic acid 8-allyl-7-nitro-2,3-dihydro-benzo(1,4)dioxin-2-ylmethyl ester 9.55 g (38.0 mmole) of (S)-(8-allyl-7-nitro-2,3-dihydro-benzo(1,4)dioxin-2-yl)-methanol was dissolved in 465 mL of pyridine, 29.0 g (152 mmole) of p-toluenesulfonyl chloride was added and the mixture stirred at room temperature under nitrogen overnight. Water was then added to quench the excess tosyl chloride and the solvent was removed in vacuum and replaced with methylene chloride. This solution was washed with 2 N HCl, with saturated sodium bicarbonate, and with saturated brine, and dried over magnesium sulfate. Filtration, evaporation in vacuum and column chromatography on silica gel with 1:1 hexane/methylene chloride as eluant gave 12.6 g (92%) of toluene-4-sulfonic acid (R)-allyl-7-nitro-2,3-benzo(1,4)dioxin-2-ylmethyl ester, which slowly crystallized to a tan solid (m.p. 60–62° C.) upon standing.

Elemental Analysis for: $C_{19}H_{19}NO_7S$ Calc'd: C, 56.29; H, 4.72; N, 3.45 Found: C, 56.13; H, 4.58; N, 3.44

Intermediate 6

{7-Nitro-8-[1-propenyl]-2,3-dihydro-1,4-benzodioxin-2-yl}methyl 4-methylbenzenesulfonate To a solution of 10.0 g (24.0 mmole) of (R)-[8-allyl-7-nitro-2,3-dihydro-1,4-benzodioxin-2-yl]methyl 4-methylbenzenesulfonate in 700 mL of benzene was added 1.03 g of bis(acetonitrile)dichloropalladium (II) and the mixture was refluxed under nitrogen for 48 hours. The catalyst was then removed by filtration and the filtrate concentrated in vacuum to a brown oil. Column chromatography on silica gel with methylene chloride as eluant gave 7.2 g of the title compound as a mixture of E and Z isomers. A sample of {(2R)-7-nitro-8[(E)-1-propenyl]-2,3-dihydro-1,4-benzodioxin-2-yl}methyl 4-methylbenzenesulfonate was obtained as a yellow solid (m.p. 105–106° C.) by evaporation of a pure E isomer-containing fraction.

Elemental Analysis for: $C_{19}H_{19}NO_7S$ Calc'd: C, 56.29; H, 4.72; N, 3.45 Found: C, 56.12; H, 4.64; N, 3.39

Intermediate 7

{7-Amino-8-[1-propenyl]-2,3-dihydro-1,4-benzodioxin-2-yl}methyl 4-methylbenzenesulfonate 10.0 g (24.0 mmole) of {(2R)-7-nitro-8-[1-propenyl]-2,3-dihydro-1,4-benzodioxin-2-yl}methyl 4-methylbenzenesulfonate and 28.0 g (123 mmole) of stannous chloride dihydrate were combined and heated to 70° C. in ethyl acetate (250 mL) for 6 hours under nitrogen. After cooling to room temperature, the reaction mixture was poured into ice and was made basic with sodium bicarbonate. It was then extracted with ethyl acetate, washed with brine, dried over magnesium sulfate, filtered and evaporated to a brown oil. The crude oil was then chromatographed on silica gel with 50% hexane/methylene chloride to remove impurities and the desired product was eluted with 0.5% methanol/$CH_2Cl_2$ to give 8.16 g (91%) of the (R)-enantiomer of the title compound as a yellow oil. For analytical purposes, 50 mg of the yellow oil was crystallized from ethanol with the addition of fumaric acid to give the fumarate of the title compound. MS (ESI) m/z 375 (M+H)+.

Elemental Analysis for: $C_{19}H_{21}NO_5S.1.00\ C_4H_4O_4$ Calc'd: C, 56.20; H, 5.13; N, 2.85 Found: C, 56.40; H, 4.99; N, 2.91

Intermediate 8

{7-{[(Benzyloxy)carbonyl]amino}-8-[1-propenyl]-2,3-dihydro-1,4-benzodioxin-2-yl}methyl 4-methylbenzenesulfonate To a solution of {(2R)-7-amino-8-[1-propenyl]-2,3-dihydro-1,4-benzodioxin-2-yl}methyl 4-methylbenzenesulfonate (4.20 g, 11.2 mmole) in ethyl acetate (150 mL) was added benzyl chloroformate (8.00 mL, 56.0 mmole). The reaction mixture was stirred under nitrogen for 0.5 hour, then a solution of N,N-diisopropylethylamine (9.75 mL, 56 mmole) in ethyl acetate (75 mL) was added dropwise over a period of 0.5 hour. The mixture was stirred at room temperature under nitrogen overnight. The reaction was diluted in volume to 350 ml and was then washed with 2N HCl (2×100 mL), saturated sodium bicarbonate (150 mL) and brine (100 mL), dried over magnesium sulfate, filtered and evaporated to an oil. The crude oil was column chromatographed on silica gel with 10% ethyl acetate/hexane to remove impurities and the product eluted with 60% ethyl acetate/hexane to give the (R)-enantiomer of the title compound as a yellow oil (4.5 g, 79%). $^1$H (CDCl$_3$) doublet 7.8 δ (2); multiplet 7.4 δ (7 H); doublet 6.7 δ (2 H); multiplet 6.0–6.2 δ (2 H); singlet 5.2 δ (2 H); multiplet 4.4 δ (1 H); multiplet 4.2 δ (3H); multiplet 4.0 δ (1 H); singlet 2.4 δ (3 H); doublet 1.9 δ (3 H).

Intermediate 9

{7-{[(Benzyloxy)carbonyl]amino}-8-formyl-2,3-dihydro-1,4-benzodioxin-2-yl}methyl 4-methylbenzenesulfonate To a solution {(2R)-7-{[(benzyloxy)carbonyl]amino}-8-[1-propenyl]-2,3-dihydro-1,4-benzodioxin-2-yl}methyl 4-methylbenzenesulfonate (4.5 g, 8.84 mmole) in tetrahydrofuran (225 mL) was added OsO$_4$ (1.65 mL, 0.270 mmole). Then a solution of NaIO$_4$ (9.45 g, 44.2 mmole) in water (100 mL) was added dropwise. The reaction was stirred at room temperature under nitrogen overnight. Water (250 mL) was added to the mixture and it was then extracted with ethyl acetate. The organic phase was then washed with brine, dried over magnesium sulfate, filtered and evaporated to 4.45 g (>95%) of the (R)-enantiomer of the title compound as a yellow solid. $^1$H (CDCl$_3$) broad singlet 10.8 δ (1 H); singlet 10.1 δ (1 H); doublet 7.9 δ (1 H); doublet 7.8 δ (2 H); multiplet 7.4 δ (7 H); doublet 7.0 δ (1 H); singlet 5.2 δ (2 H); multiplet 4.5 δ (1 H); multiplet 4.2 δ (3 H); multiplet 4.1 δ (1 H); singlet 2.4 δ (3 H).

Intermediate 10

{7-{[(Benzyloxy)carbonyl]amino}-8-hydroxy-2,3-dihydro-1,4-benzodioxin-2-yl}methyl 4-methylbenzenesulfonate A solution of {(2R)-7-{[(benzyloxy)carbonyl]amino}-8-formyl-2,3-dihydro-1,4-benzodioxin-2-yl}methyl 4-methylbenzenesulfonate (4.45 g, 8.95 mmole) in methylene chloride (50 mL) was added dropwise to a solution of m-chloroperoxybenzoic acid (6.45 g, 22.4 mmole) in methylene chloride (120 mL). The reaction was stirred under nitrogen overnight. After dilution to 300 mL in volume, it was washed with saturated sodium bicarbonate (2×200 mL), brine (100 mL), dried over magnesium sulfate, filtered and evaporated to dryness. A H$^1$NMR spectra was taken of the crude product and it was determined to be the formate ester. Cleavage was effected by stirring in methanol over basic alumina overnight. After filtration and evaporation, the product was purified by column chromatography on silica gel with hexane to remove the impurities, and the product eluted with methylene chloride to give the (R)-enantiomer of the title compound as a yellow oil (1.80 g, 40%). $^1$H (CDCl$_3$) doublet 7.8 δ (2 H); multiplet 7.2–7.4 δ (7 H); broad singlet 7.0 δ (1 H); doublet 6.4 δ (1 H); singlet 5.2 δ (2 H); multiplet 4.4 δ (1 H); multiplet 4.2 δ (3 H); multiplet 4.0 δ (1 H); singlet 2.4 δ (3 H).

Intermediate 11

[7-Amino-8-hydroxy-2,3-dihydro-1,4-benzodioxin-2-yl]methyl 4-methylbenzenesulfonate A mixture of (2R)-7-{[(benzyloxy)carbonyl]amino}-8-hydroxy-2,3-dihydro-1,4-benzodioxin-2-yl}methyl 4-methylbenzenesulfonate (1.8 g, 3.7 mmole) and 0.25 g of 10% palladium on carbon in 200 mL of methanol was treated with 40 psi of hydrogen on a Parr shaker for 3 hours. The catalyst was filtered and washed with additional methanol. The solvent was evaporated in vacuum to yield 1.25 g (87%) of the (R)-enantiomer of the hydrochloride hemihydrate of the title compound as a beige foam.

Elemental Analysis for: $C_{16}H_{17}NO_6S.1.00\ HCl.0.5\ H_2O$ Calc'd: C, 48.43; H, 4.83; N, 3.53 Found: C, 48.21; H, 4.34; N, 3.58

Intermediate 12

7,8-Dihydro[1,4]dioxino[2,3-g][1,3]benzoxazol-8-ylmethyl 4-methylbenzenesulfonate

[(2R)-7-Amino-8-hydroxy-2,3-dihydro-1,4-benzodioxin-2-yl]methyl 4-methyl-benzenesulfonate hydrochloride (1.05 g, 2.99 mmole) in trimethyl orthoformate (7 mL) was heated to reflux in the presence of 0.20 g of p-toluenesulfonic acid for 3 hours. The solvent was removed under high vacuum to yield a beige solid. The crude product was recrystallized from ethanol to give 0.81 g (75%) of the (R)-enantiomer of the title compound, MS (ESI) m/z 361 (M+H)+.

Elemental Analysis for: $C_{17}H_{15}NO_5S$ Calc'd: C, 56.50; H, 4.18; N, 3.88 Found: C,56.10; H, 4.37; N, 3.69

Intermediate 13

1-[5-Hydroxy-3-(hydroxymethyl)-2,3-dihydro-1,4-benzodioxin-6-yl]-1-ethanone

To a solution of 2',3',4'-trihydroxyacetophenone (10.6 g, 63.0 mmole) in DMF (75 mL) was added potassium carbonate (17.4 g, 126 mmole). After 5 minutes (R)-glycidyl tosylate (9.67 g, 42.3 mmole) was added, then the heterogeneous mixture was heated to 70° C. for 3 hours. After removal of the solvent in vacuum, the residue was taken into water (800 mL) and was then extracted with ethyl acetate (4×300 mL). The combined organic layers were dried over magnesium sulfate, filtered and evaporate to dryness in vacuum. The crude brown oil thus obtained was column chromatographed on silica gel with 40% hexane/ethyl acetate as eluant to give the (S)-enantiomer of the title compound as a yellow oil which solidifies upon standing (7.5 g, 78%). MS (ESI) m/z 223 (M−H)−.

Elemental Analysis for: $C_{11}H_{12}O_5.0.10\ H_2O$ Calc'd: C, 58.46; H, 5.44 Found: C, 58.02; H, 5.09

Intermediate 14

1-[5-Hydroxy-3-(hydroxymethyl)-2,3-dihydro-1,4-benzodioxin-6-yl]-1-ethanone oxime A solution of hydroxylamine hydrochloride (2.38 g, 34.2 mmole) in 1:1 ethanol/pyridine (100 mL) was added to a solution of 1-[(3S)-5-hydroxy-3-(hydroxy-methyl)-2,3-dihydro-1,4-benzodioxin-6-yl]-1-ethanone (1.92 g, 8.57 mmole) in ethanol (200 mL). It was then heated to reflux under nitrogen for 5 hours. Upon cooling, the solvent was removed and replaced with ethyl acetate. The solution was then washed with water (200 mL) and with aqueous 2N HCl (100 mL), dried over magnesium sulfate, filtered and evaporated in vacuum to give 1.89 g (93%) of the (S)-enantiomer of the title compound as a gray solid, m.p. 162° C. MS (ESI) m/z 240 (M+H)+.

Elemental Analysis for: $C_{11}H_{13}NO_5.0.35\ H_2O$ Calc'd: C, 53.81; H, 5.62; N, 5.71 Found: C, 53.51; H, 5.30; N, 5.58

Intermediate 15

[2-Methyl-7,8-dihydro[1,4]dioxino[2,3-g][1,3]benzoxazol-8-yl]methanol 3.03 g (12.6 mmole) of 1-[(3S)-5-hydroxy-3-(hydroxymethyl)-2,3-dihydro-1,4-benzodioxin-6-yl]-1-ethanone oxime was dissolved in a mixture of 1:3 N,N-dimethylacetamide/acetonitrile (100 mL). The solution was cooled in an ice/water bath and a solution of phosphorus oxychloride (1.26 mL, 35 mmole) in 1:3 N,N-dimethylacetamide/acetonitrile (30 mL) was added. The reaction mixture was stirred under nitrogen over a period of 48 hours. It was then added to an ice cold, saturated solution of sodium acetate, extracted with ethyl acetate, dried over magnesium sulfate, filtered and evaporated in vacuum. The resulting crude oil was column chromatographed on silica gel with 60% hexane/ethyl acetate to remove impurities and the product eluted with 40% hexane/ethyl acetate. After evaporation of the solvent in vacuum, 2.08 g (75%) of the (S)-enantiomer of the title compound was obtained as a white solid, m.p. 120° C. MS (ESI) m/z 222 (M+H)+.

Elemental Analysis for: $C_{11}H_{11}NO_4.0.20\ H_2O$ Calc'd: C, 58.77; H, 5.11; N, 6.23 Found: C, 58.93; H, 4.91; N, 6.14

Intermediate 16

[2-Methyl-7,8-dihydro[1,4]dioxino[2,3-g][1,3]benzoxazol-8-yl]methyl 4-methylbenzenesulfonate To a solution of [(8S)-2-methyl-7,8-dihydro[1,4]dioxino[2,3-g][1,3]-benzoxazol-8-yl]methanol (1.80 g, 8.14 mmole) in methylene chloride (100 mL) was added p-toluenesulfonyl chloride (3.90 g, 20.4 mmole). The mixture was cooled in an ice bath and a solution of diisopropylethylamine (3.55 mL, 20.4 mmole) in methylene chloride (20 mL) was then added dropwise, followed by 4-dimethylaminopyridine (0.65 g, 5.30 mmole). The solution was allowed to warm to room temperature and was stirred under nitrogen overnight. The reaction was diluted to 500 mL in volume with methylene chloride, then washed with aqueous 2 N HCl (200 mL), with saturated aqueous sodium bicarbonate (200 mL), and with brine (150 mL), dried over magnesium sulfate, filtered and evaporated in vacuum to a yellow oil. The crude oil was column chromatographed on silica gel using methylene chloride to remove impurities and 3% methanol/methylene chloride to elute the (R)-enantiomer of the title compound, which becomes a white solid under vacuum (2.56 g, 84%), m.p. 123° C. MS (ESI) m/z 376 (M+H)+.

Elemental Analysis for: $C_{18}H_{17}NO_8S.0.20\ H_2O$ Calc'd: C, 57.04; H, 4.63; N, 3.70 Found: C, 56.75; H, 4.62; N, 3.51

EXAMPLE 1

8-(2-Methyl-7,8-dihydro-1,6,9-trioxa-3-aza-cyclopenta[a]naphthalen-8-ylmethyl)-1-phenyl-1,3,8triazaspiro[4.5]decan-4-one (8R)-7,8-Dihydro[1,4]dioxino[2,3-g][1,3]benzoxazol-8-ylmethyl 4-methyl-benzenesulfonate (0.79 g, 2.1 mmole) and 1-phenyl-1,3,8-triazaspiro[4.5]-decan-4-one (1.46 g, 6.3 mmole) were combined in 40 mL of DMSO under nitrogen. This solution was heated to 75–80° C. under nitrogen for 4 hours. After completion, the reaction was cooled to room temperature and partitioned between ethyl acetate and saturated aqueous sodium bicarbonate. The organic phase was washed with brine, dried over magnesium sulfate and concentrated in vacuum. The crude oil was column chromatographed on silica gel using first methylene chloride to remove impurities and then 1% methanol/methylene chloride to elute 0.62 g of the desired free amine. This was recrystallized from ethanol with the addition of 0.20 g of fumaric acid to give 0.40 g of the (S)-enantiomer of the title compound as a white solid, m. p. 240° C.

Elemental Analysis for: $C_{24}H_{26}N_4O_4 \cdot 0.50\ C_4H_4O_4 \cdot 0.10\ H_2O$ Calc'd: C, 63.17; H, 5.75; N, 11.33 Found: C, 62.98; H, 5.48; N, 11.18

EXAMPLE 2

1-[1-(2-Methyl-7,8-dihydro-1,6,9-trioxa-3-aza-cyclopenta[a]naphthalen-8-ylmethyl)-piperidin-4-yl]-1,3-dihydro-2H-benzimidazol-2-one (8R)-2-Methyl-7,8-dihydro[1,4]dioxino[2,3-g][1,3] benzoxazol-8-ylmethyl 4-methylbenzenesulfonate (0.43 g, 1.14 mmole) and 4-(2-keto-1-benzimidazolinyl)-piperidine (0.77 g, 3.54 mmole) were combined in 10 mL of DMSO under nitrogen. This solution was heated to 82° C. under nitrogen for 4 hours. After completion, the reaction was allowed to cool to room temperature and was partitioned between ethyl acetate and saturated aqueous sodium bicarbonate. The organic phase was washed with brine, dried over sodium sulfate and concentrated in vacuum. The resulting crude oil was column chromatographed on silica gel using first methylene chloride to remove impurities and then 1% methanol/methylene chloride to elute 0.4 g of the (S)-enantiomer of the title compound, m.p. 218–220° C.

Elemental Analysis for: $C_{23}H_{24}N_4O_4$ Calc'd: C, 65.7; H, 5.75; N, 13.32 Found: C, 65.47; H, 5.6; N, 13.13

EXAMPLE 3

1-(2-Methyl-7,8-dihydro-1,6,9-trioxa-3-aza-cyclopenta[a]naphthalen-8-ylmethyl)-4-[3-(trifluoromethyl)phenyl]-4-piperidinol (8R)-2-Methyl-7,8-dihydro[1,4]dioxino[2,3-g][1,3] benzoxazol-8-ylmethyl 4-methylbenzenesulfonate (0.43 g, 1.14 mmole) and 4-[3-(trifluoromethyl)phenyl]-4-piperidinol (0.84 g, 3.43 mmole) were combined in 10 mL of DMSO under nitrogen. This solution was heated to 80° C. under nitrogen for 4 hours. After completion, the reaction was allowed to cool to room temperature and was partitioned between ethyl acetate and saturated aqueous sodium bicarbonate. The organic phase was washed with brine, dried over magnesium sulfate and concentrated in vacuum. The resulting crude oil was column chromatographed on silica gel using first methylene chloride to remove impurities and then 1% methanol/methylene chloride to elute 0.33 g of the (S)-enantiomer of the title compound, m.p. 148–151° C.

Elemental Analysis for: $C_{23}H_{23}F_3N_2O_4$ Calc'd: C, 61.6; H, 5.17; N, 6.25 Found: C, 61.55; H, 5.06; N, 5.98

EXAMPLE 4

(4-Fluorophenyl) (1-[2-methyl-7,8-dihydro-1,6,9-trioxa-3-aza-cyclopenta[a]naphthalen-8-ylmethyl]-4-piperidinyl)methanone (8R)-2-Methyl-7,8-dihydro[1,4]dioxino[2,3-g][1,3] benzoxazol-8-ylmethyl 4-methylbenzenesulfonate (0.45 g, 1.2 mmole) and 4-(4-fluorobenzoyl)piperidine (0.73 g, 3.54 mmole) were combined in 10 mL of DMSO under nitrogen. This solution was heated to 80° C. under nitrogen for 4 hours. After completion, the reaction was cooled to room temperature and partitioned between ethyl acetate and saturated aqueous sodium bicarbonate. The organic phase was washed with brine, dried over magnesium sulfate and concentrated in vacuum. The resulting crude oil was column chromatographed on silica gel using first methylene chloride to remove impurities and then 1% methanol/methylene chloride to elute 0.28 g of the (S)-enantiomer of the title compound. This was recrystallized from ethanol with the addition of one equivalent of fumaric acid to give 0.30 g of pale yellow solid, m.p. 229–230° C.

Elemental Analysis for: $C_{23}H_{23}FN_2O_4 \cdot C_4H_4O_4$ Calc'd: C, 61.59; H, 5.17; N, 5.32 Found: C, 61.27; H, 5; N, 5.23

EXAMPLE 5

2-Methyl-8-{[4-phenyl-3,6-dihydro-1(2H)-pyridinyl] methyl}-7,8-dihydro-1,6,9-trioxa-3-aza-cyclopenta[a]naphthalene (8R)-2-Methyl-7,8-dihydro[1,4]dioxino[2,3-g][1,3] benzoxazol-8-ylmethyl 4-methylbenzenesulfonate (0.40 g, 1.1 mmole) and 4-(3-trifluoromethyl-phenyl)-1,2,3,6-tetrahydro-pyridine (0.35 g, 1.54 mmole) were combined in 5 mL of DMF and 5 ml of THF under nitrogen. This solution was refluxed under nitrogen for overnight. After completion, the reaction was cooled to room temperature and partitioned between ethyl acetate and saturated aqueous sodium bicarbonate. The organic phase was washed with brine, dried over magnesium sulfate and concentrated in vacuum. The resulting crude oil was column chromatographed on silica gel using first methylene chloride to remove impurities and then 1% methanol/methylene chloride to elute the (S)-enantiomer of the title compound. This was recrystallized from ethanol with the addition of one equivalent of fumaric acid to give 80 mg of white solid, m.p. 170–173° C.

Elemental Analysis for: $C_{23}H_{21}F_3N_2O_3 \cdot C_4H_4O_4$ Calc'd: C, 59.34; H, 4.61; N, 5.13 Found: C, 59.38; H, 4.41; N, 4.95

EXAMPLE 6

2-Methyl-8-(piperidin-1-ylmethyl)-7,8-dihydro-1,6,9-trioxa-3-aza-cyclopenta[a]naphthalene (8R)-2-Methyl-7,8-dihydro[1,4]dioxino[2,3-g][1,3] benzoxazol-8-ylmethyl 4-methylbenzenesulfonate (0.38 g, 1 mmole) and piperidine 15 ml were combined and heated at 80° C. under nitrogen for 4 hours. After completion, piperidine was removed under vacuum and the residue was partitioned between ethyl acetate and saturated aqueous sodium bicarbonate. The organic phase was washed with brine, dried over magnesium sulfate and concentrated in vacuum. The crude oil was column chromatographed on silica gel using first methylene chloride to remove impurities and then 1% methanol/methylene chloride to elute the (S)-enantiomer of the title compound. This was recrystallized from ethanol with the addition of one equivalent of fumaric acid to give 0.24 g of white solid, m.p. 109–112° C.

Elemental Analysis for: $C_{16}H_{20}N_2O_3 \cdot C_4H_4O_4$ Calc'd: C, 59.4; H, 5.98; N, 6.93 Found: C, 59.02; H, 6.13; N, 6.82

What is claimed is:

1. A compound of formula I:

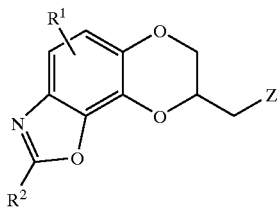

wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidinyl, piperidinyl, homopiperidinyl, morpholinyl, thiomorpholinyl,

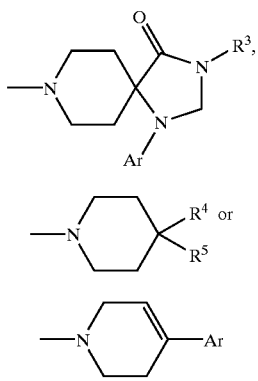

$R^3$ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl;

$R^4$ is hydroxy, cyano or carboxamido and $R^5$ is Ar; or $R^4$ is hydrogen and $R^5$ is benzoyl, 1-benzimidazol-2-onyl, benzoisothiazolyl, benzisoxazolyl, or —(CH$_2$)$_m$Q;

m is 0 to 4; and

Q is Ar,

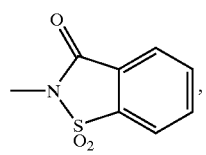

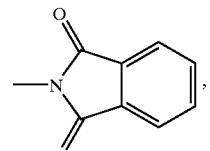

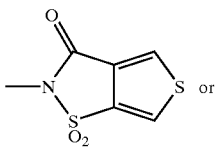

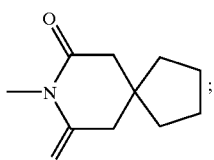

or a pharmaceutically acceptable salt thereof, wherein said phenyl, naphthyl, pyrimidinyl, pyrazinyl, furyl, thienyl, 1-benzimidazol-2-onyl, benzoisothiazolyl, or benzisoxazolyl groups are optionally substituted with substituents selected from hydrogen, halo, cyano, carboxamido, carboalkoxy of two to six carbon atoms, trifluoromethyl, alky of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

2. A compound of claim 1 wherein Z is a radical of formula II or III.

3. A compound of claim 1 wherein $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atoms and Z is a radical of formula II.

4. A compound of claim 3 wherein $R^1$ is hydrogen, halo, trifluoromethyl, alkyl of one to six carbon atoms or alkoxy of one to six carbon atoms and $R^2$ is hydrogen, trifluoromethyl or alkyl of one to six carbon atoms.

5. A compound of claim 1 wherein $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atoms; Z is a radical of formula III, $R^4$ is hydroxy and $R^5$ is Ar.

6. A compound of claim 5 wherein $R^1$ is hydrogen, halo, trifluoromethyl, alkyl of one to six carbon atoms or alkoxy of one to six carbon atoms and $R^2$ is hydrogen, trifluoromethyl or alkyl of one to six carbon atoms.

7. A compound of claim 1 wherein $R^1$ is hydrogen, halo, trifluoromethyl, alkyl of one to six carbon atoms, alkoxy of one to six carbon atoms, amino, mono- or di-alkylamino in which each alkyl group has one to six carbon atoms; $R^2$ is hydrogen, trifluoromethyl, amino, mono- or di-alkylamino in which each alkyl group has one to six carbon atoms, or alkyl of one to six carbon atom; Z is a radical of formula III, R⁴ is hydrogen and R⁵ is benzoyl, 1-benzimidazol-2-onyl, benzoisothiazolyl, benzisoxazolyl, each optionally substituted, or —(CH₂)ₘQ.

8. A compound of claim 7 wherein R¹ is hydrogen, halo, trifluoromethyl, alkyl of one to six carbon atoms or alkoxy of one to six carbon atoms; R² is hydrogen, trifluoromethyl or alkyl of one to six carbon atoms, and m is 0 or 1.

9. The compound of claim 1 which is 8-(2-methyl-7,8-dihydro-1,6,9-trioxa-3-aza-cyclopenta[a]naphthalen-8-ylmethyl)-1-phenyl-1,3,8-triazaspiro[4.5]decan-4-one or a pharmaceutically acceptable salt thereof.

10. The compound of claim 1 which is 1-[1-(2-methyl-7,8-dihydro-1,6,9-trioxa-3-aza-cyclopenta[a]naphthalen-8-ylmethyl)-piperidin-4-yl]-1,3-dihydro-2H-benzimidazol-2-one or a pharmaceutically acceptable salt thereof.

11. The compound of claim 1 which is 1-(2-methyl-7,8-dihydro-1,6,9-trioxa-3-aza-cyclopenta[a]naphthalen-8-ylmethyl)-4-[3-(trifluoromethyl)phenyl]-4-piperidinol or a pharmaceutically acceptable salt thereof.

12. The compound of claim 1 which is (4-fluorophenyl)(1-[2-methyl-7,8-dihydro-1,6,9-trioxa-3-aza-cyclopenta[a]naphthalen-8-ylmethyl]-4-piperidinyl)methanone or a pharmaceutically acceptable salt thereof.

13. The compound of claim 1 which is 2-methyl-8-{[4-(3-trifluoromethyl)phenyl-3,6-dihydro-1(2H)-pyridinyl]methyl}-7,8-dihydro-1,6,9-trioxa-3-aza-cyclopenta[a]-naphthalene or a pharmaceutically acceptable salt thereof.

14. The compound of claim 1 which is 2-methyl-8-(piperidin-1-ylmethyl)-7,8-dihydro-1,6,9-trioxa-3-aza-cyclopenta[a]naphthalene or a pharmaceutically acceptable salt thereof.

15. A method of treating a subject suffering from a condition selected group consisting of anxiety, aggression and stress which comprises providing to the subject suffering from said condition, a therapeutically effective amount of a compound of formula I

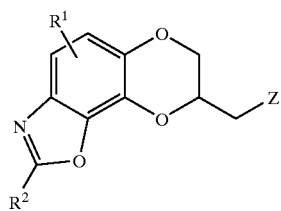

wherein

R¹ is hydrogen, halo, cyano, caboxamido, carboalkyoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

R² is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidinyl, piperidinyl, homopiperidinyl, morpholinyl, thiomorpholinyl,

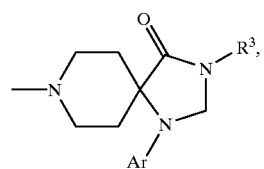

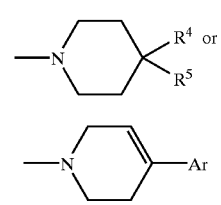

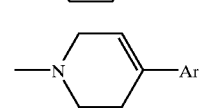

R³ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl;

R⁴ is hydroxy, cyano or carboxamido and R⁵ is Ar; or

R⁴ is hydrogen and R⁵ is benzoyl, 1-benzimidazol-2onyl, benzoisothiazolyl, benzisoxazolyl, or —(CH₂)ₘQ;

m is 0 to 4; and

Q is Ar,

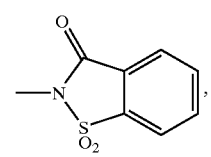

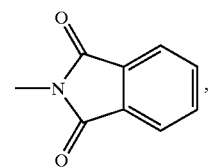

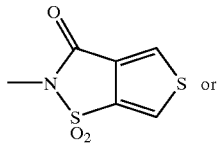

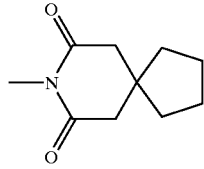

or a pharmaceutically acceptable salt thereof, wherein said phenyl, naphthyl, pyridinyl, pyrimidinyl, pyrazinyl, furyl, thienyl, 1-benzimidazol-2-onyl, benzoisothiazoyl, or benzisoxazoyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

16. The method of claim 15 wherein the subject is a human.

17. A method of treating a subject suffering from a condition selected from the group consisting of eating disorders, disorders of thermoregulation, sleep dysfunction and sexual dysfunction which comprises providing to the subject suffering from said condition, a therapeutically effective amount of a compound of formula I:

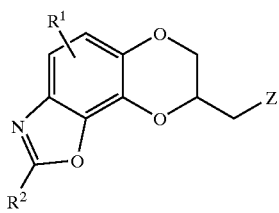

wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidinyl, piperidinyl, homopiperidinyl, morpholinyl, thiomorpholinyl,

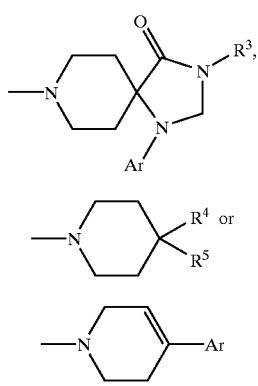

$R^3$ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl;

$R^4$ is hydroxy, cyano or carboxamido and $R^5$ is Ar; or $R^4$ is hydrogen and $R^5$ is benzoyl, 1-benzimidazol-2-onyl, benzoisothiazolyl, benzisoxazolyl, or $-(CH_2)_mQ$;

m is 0 to 4; and

Q is Ar,

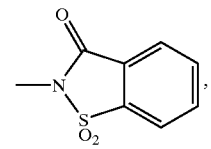

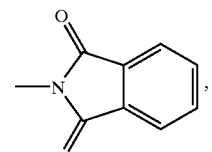

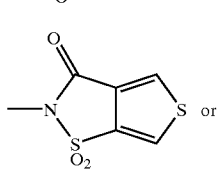

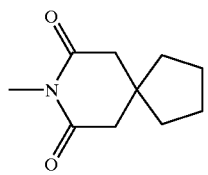

or a pharmaceutically acceptable salt thereof;

wherein said phenyl, naphthyl, pyridinyl, pyrimidinyl, pyrazinyl, furyl, thienyl, 1-benzimidazol-2-onyl, benzoisothiazoyl, or benzisoxazoyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

18. The method of claim 17 wherein the subject is a human.

19. A method of treating a subject suffering depression comprising providing to the subject suffering from said condition, an antidepressant amount of a serotonin selective reuptake inhibitor and an amount of a compound of formula I:

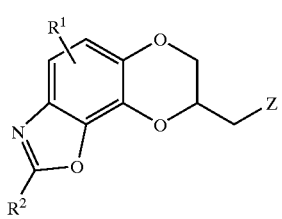

wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidinyl, piperidinyl, homopiperidinyl, morpholinyl, thiomorpholinyl,

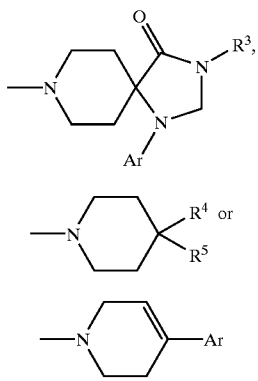

II

III

IV $R^3$ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl;

$R^4$ is hydroxy, cyano or carboxamido and $R^5$ is Ar; or $R^4$ is hydrogen and $R^5$ is benzoyl, 1-benzimidazol-2-onyl, benzoisothiazolyl, benzisoxazolyl, or —$(CH_2)_mQ$;

m is 0 to 4; and

Q is Ar,

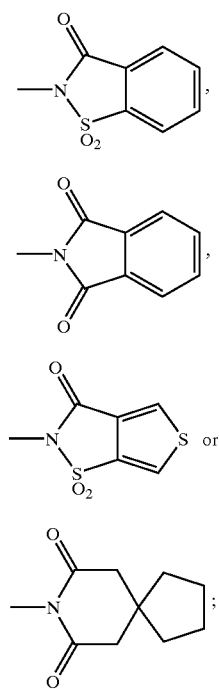

V

VI

VII

VIII or a pharmaceutically acceptable salt thereof, wherein said phenyl, naphthyl, pyridinyl, pyrimidinyl, pyrazinyl, furyl, thienyl, 1-benzimidazol-2-onyl, benzoisothiazoyl, or benzisoxazoyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

said amount being effective to increase the onset of antidepressant efficacy.

20. The method of claim 19 wherein the subject is a human.

21. The method of claim 19 wherein the serotonin selective reuptake inhibitor is sertraline, fluvoxamine, paroxetine, venlafaxine, duloxetine, citalopram, fluoxetine or metabolites thereof.

22. A pharmaceutical composition comprising a compound of formula I:

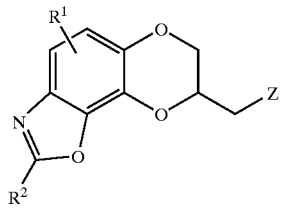

I wherein $R^1$ is hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms;

$R^2$ is hydrogen, halo, trifluoromethyl, amino, mono- or di-alkylamino in which each alkyl group has 1 to 6 carbon atoms, alkoxy of one to six carbon atoms or alkyl of one to six carbon atoms;

Z is pyrrolidinyl, piperidinyl, homopiperidinyl, morpholinyl, thiomorpholinyl,

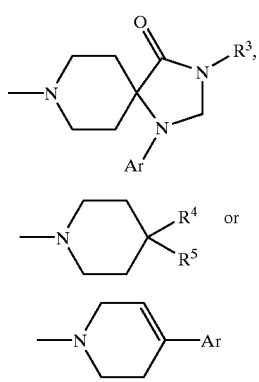

II

III

IV $R^3$ is hydrogen, alkyl of 1 to 6 carbon atoms, alkenyl of 3 to 6 carbon atoms or alkynyl or 3 to 6 carbon atoms;

Ar is phenyl, pyridinyl, pyrimidinyl, pyrazinyl, furyl, or thienyl;

$R^4$ is hydroxy, cyano or carboxamido and $R^5$ is Ar; or $R^4$ is hydrogen and $R^5$ is benzoyl, 1-benzimidazol-2-onyl, benzoisothiazolyl, benzisoxazolyl, or —$(CH_2)_mQ$;

m is 0 to 4; and
Q is Ar,

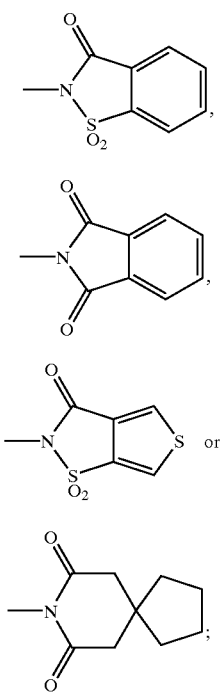

or a pharmaceutically acceptable salt thereof;
wherein said phenyl, naphthyl, pyridinyl, pyrimidinyl, pyrazinyl, furyl, thienyl, 1-benzimidazol-2-onyl, benzoisothiazoyl, or benzisoxazoyl groups are optionally substituted with substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.
and a pharmaceutically acceptable carrier or excipient.

23. The composition of claim 22 further comprising an antidepressant amount of a serotonin selective reuptake inhibitor.

24. The composition of claim 23 wherein the serotonin selective reuptake inhibitor is sertraline, fluvoxamine, paroxetine, venlafaxine, duloxetine, citalopram, fluoxetine or metabolites thereof.

25. A compound of claim 1 wherein at least one of said phenyl, pyridinyl, pyrimidinyl, pyrazinyl, furyl, thienyl, 1-benzimidazol-2-onyl, benzoisothiazoyl, or benzisoxazoyl bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

26. A compound of claim 15 wherein at least one of said phenyl, pyridinyl, pyrimidinyl, pyrazinyl, furyl, thienyl, 1-benzimidazol-2-onyl, benzoisothiazoyl, or benzisoxazoyl bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

27. A compound of claim 17 wherein at least one of said phenyl, pyridinyl, pyrimidinyl, pyrazinyl, furyl, thienyl, 1-benzimidazol-2-onyl, benzoisothiazoyl, or benzisoxazoyl bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

28. A compound of claim 19 wherein at least one of said phenyl, pyridinyl, pyrimidinyl, pyrazinyl, furyl, thienyl, 1-benzimidazol-2-onyl, benzoisothiazoyl, or benzisoxazoyl bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

29. A compound of claim 22 wherein at least one of said phenyl, pyridinyl, pyrimidinyl, pyrazinyl, furyl, thienyl, benzoyl, 1-benzimidazol-2-onyl, benzoisothiazoyl, or benzisoxazoyl bears 1 to 3 substituents selected from hydrogen, halo, cyano, carboxamido, carboalkoxy of two to six carbon atoms, trifluoromethyl, alkyl of 1 to 6 carbon atoms, alkoxy of 1 to 6 carbon atoms, alkanoyloxy of 2 to 6 carbon atoms, amino, mono- or di-alkylamino in which each alkyl group has 1 to 6 carbon atoms, alkanamido of 2 to 6 carbon atoms, or alkanesulfonamido of 1 to 6 carbon atoms.

* * * * *